United States Patent [19]

Matsuura et al.

[11] Patent Number: 4,840,932

[45] Date of Patent: Jun. 20, 1989

[54] CATALYST FOR PRODUCING 1,4-NAPHTHOQUINONE

[75] Inventors: Ryo Matsuura, Yamato; Shigeyuki Yoshimura, Tokyo; Yasuo Asanuma, Kamakura; Katsuaki Nasu, Yokohama; Haruo Yoshizumi, Tokyo; Kazumi Tsujimoto, Hatano; Toshiyuki Kimura, Yokohama, all of Japan

[73] Assignee: Kawasaki Kasei Chemicals Ltd., Tokyo, Japan

[21] Appl. No.: 170,057

[22] Filed: Mar. 16, 1988

Related U.S. Application Data

[63] Continuation of Ser. No. 748,714, Jun. 26, 1985, abandoned, which is a continuation of Ser. No. 176,683, Aug. 8, 1980, abandoned.

[30] Foreign Application Priority Data

Sep. 5, 1979 [JP] Japan .................................. 54-112797

[51] Int. Cl.$^4$ ...................... B01J 23/04; B01J 23/22; B01J 35/02
[52] U.S. Cl. .................................. 502/202; 502/209; 502/218; 502/527
[58] Field of Search ................ 502/209, 218, 527, 202

[56] References Cited

U.S. PATENT DOCUMENTS

| | | | |
|---|---|---|---|
| 2,989,544 | 6/1961 | Saunders et al. ............... | 260/396 R |
| 3,232,955 | 2/1966 | Nonnenmacher et al. ...... | 260/396 R |
| 3,347,798 | 10/1967 | Baer et al. ........................ | 252/477 R |
| 3,402,187 | 9/1968 | Kaiser et al. ..................... | 260/396 R |
| 3,898,180 | 8/1975 | Crooks et al. ................... | 252/477 R |
| 4,035,399 | 7/1977 | Yokoyama et al. ............. | 260/396 R |
| 4,036,783 | 7/1977 | Blechschmitt et al. ............. | 252/461 |

FOREIGN PATENT DOCUMENTS

317979 1/1920 Fed. Rep. of Germany .

*Primary Examiner*—W. J. Shine
*Attorney, Agent, or Firm*—Oblon, Fisher, Spivak, McClelland & Maier

[57] ABSTRACT

A process for producing 1,4-naphthoquinone by oxidizing naphthalene with molecular oxygen in a vapor phase in the presence of a catalyst. The catalyst is made of a mixture of a carrier and fusible catalytic components including vanadium oxide and alkali metal sulfate and pyrosulfate, and has a molded configuration having one or more through-holes.

8 Claims, No Drawings

CATALYST FOR PRODUCING 1,4-NAPHTHOQUINONE

This application is a continuation of application Ser. No. 748,714, filed on June 26, 1985, now abandoned, which is a continuation of application Ser. No. 176,683, filed Aug. 8, 1980, now abandoned.

BACKGROUND OF THE INVENTION 1. FIELD OF THE INVENTION

The present invention relates to a process for producing 1,4-naphthoquinone. More particularly, it relates to an improved process for producing 1,4-naphthoquinone by a vapor phase catalytic oxidation of napthalene comprising passing naphthalene and a molecular oxygen-containing gas through a fixed catalyst bed of a vanadium oxide type catalyst. 2. DESCRIPTION OF THE PRIOR ARTS It has been known to use a catalyst obtained by supporting catalytic components of (1) vanadium oxide, (2) an alkali metal sulfate and (3) an alkali metal pyrosulfate on a carrier such as silicon oxide as an improved catalyst in a process for producing 1,4-naphthoquinone. Thus, a satisfactory result has not been obtained in view of a conversion of naphthalene, an yield of 1,4-naphthoquinone and a space time yield. The reason is as follows. 1,4-Naphthoquinone is an intermediate as a preliminary oxidized product of naphthalene. When a catalyst for imparting high conversion of naphthalene is used, a conversion of 1,4-naphthoquinone to phthalic anhydride as a sequential reaction is also high. In view of industrial production, it is desired to obtain a high yield of 1,4-naphthoquinone and a smaller amount of the unreacted naphthalene.

SUMMARY OF THE INVENTION

It is an object of the present invention to provide a process for producing 1,4-naphthoquinone by an oxidation of naphthalene while reducing a subsequent conversion of 1,4-naphthoquinone into phthalic anhydride and reducing the amount of the unreacted naphthalene.

The foregoing and other objects of the present invention have been attained by producing 1,4-naphthoquinone by an oxidation of naphthalene with molculate oxygen in the presence of a catalyst obtained by molding a mixture of catalytic component and a carrier in a configuration having one or more major through-hole. The mixture of the catalytic components preferably include (1) vanadium oxide, (2) an alkali metal sulfate and/or phosphate and (3) an alkali metal pyrosulfate and the carrier is preferably an inert inorganic carrier such as silicon oxide. The alkali metal sulfate should be incorporated even through the alkali metal phosphate is incorporated.

DETAILED DESCRIPTION OF THE PREFERRED EMBODIMENTS

The inventors have known that a catalyst made of silicon oxide as a carrier and vanadium oxide, an alkali metal sulfate and an alkali metal pyrosulfate as catalytic components has many fine pores in the catalyst pellet and the oxidation of naphthalene is performed on a surface of the fine pores. The oxidation is performed not only on the outer surface of the catalyst, but also on the inner surface of the catalyst.

With regard to a catalyst for producing 1,4-naphthoquinone, it is important to prevent a sequential reaction of 1,4-naphthoquinone as the preliminary oxidized product. Therefore, it is not preferable to provide longer passage of the fine pores by increasing the size of the catalyst. It is preferable to provide larger outer surface area of the catalyst per unit weight of the catalyst to obtain greater conversion of naphthalene, less sequential conversion of 1,4-naphthoquinone into phthalic anhydride and higher selectivity to 1,4-naphthoquinone.

The feature of the present invention is to provide large outer surface area per unit weight of the catalyst so as to shorten length of passages of fine pores. In order to shorten the passages of the fine pores, it has been considered to decrease the diameter of the molded catalyst. This is the simple method, however, when the molded catalyst having a small diameter is packed in a reaction tube, resistance for passing the gas through the packed layer (gas permeability) is remarkably increased to be disadvantageous for industrial production.

In accordance with the present invention, the molded catalyst having one or more major through-hole which is obtained by molding a mixture of a carrier and the catalytic components of vanadium oxide, an alkali metal sulfate and an alkali metal pyrosulfate is used. The resistance for passing the gas through the packed layer can be lowered and an outer surface area of the molded catalyst per unit weight of the catalyst can be greater and the length of the passages of the fine pores in the catalyst can be shortened whereby the activity of the catalyst per unit weight can be increased and a selectivity to 1,4-naphthoquinone can be increased. Therefore, the productivity of 1,4-naphthoquinone per unit weight of the catalyst can be removably increased and the amount of the catalyst can be saved in view of the space time yield.

The configuration of the catalyst pellet of the present invention can be tablet, cylinder, elliptic cylinder, sphere, elliptic sphere, polyhedron, polygonal cylinder, and other desired shape which has one or more through-hole as a passage for the gas.

An average length and an outer diameter of the pellet are selected depending upon a diameter of a reaction tube and preferably in a range of 2 to 20 mm, especially, 3 to 10 mm. When it is less than 3 mm, a resistance of the packed layer of the catalyst for passing the gas (gas permeability) is too large to use it in the commercial production. A ratio of a sectional area of the through-hole to a sectional area of the pellet is preferably in a range of 0.02 to 0.45 especially 0.04 to 0.35. A ratio of a volume of the through-hole to a volume of the shell is preferably in a range of 0.02 to 0.82 especially 0.04 to 0.54.

The minimum diameter of the through-hole should be a size for easily passing the gas for oxidation through the through-hole. In view of an industrial preparation, a diameter of the through-hole is preferably more than about 1 mm. The number of the through-holes in one pellet can be one or more and is not critical and is preferably one or two. The maximum diameter of the through-hole is to give a thickness of the shell of the pellet so as to be durable to mechanical shock, for example, a diameter of the through-hole of about 2 mm less than that of the outer diameter. A sectional view of the throughhole can be circle, elliptic circle, rectangle etc.

The important factor of the through-hole is to give a larger outer surface area of the pellet with a durability to mechanical shock.

The catalytic components used in the present invention can be those of the known catalyst for the production of 1,4-naphthoquinone. The catalysts made of such catalytic components are disclosed in Japanese Examined Patent Publication No. 22559/1978. The catalyst of the present invention comprises vanadium oxide as the indispensable catalytic component though other metal oxides can be incorporated together with vanadium oxide. The other metal oxides incorporated together with vanadium oxide include oxides of a metal such as aluminum, tungsten, molybdenum, tin, antimony, titanium, zirconium, chromium, manganese, cobalt, nickel, lead, zinc, niobium, tantalum, cerium, thulium, bismuth and boron. A molar ratio of the other metal oxide to vanadium oxide should be less than 2.

The source for vanadium oxide can be any vanadium compounds which can be converted into $V_2O_5$ by a calcination, and include vanadium oxides, ammonium vanadate, vanadium sulfate and vanadium oxalate.

The alkali metal in the alkali metal sulfate, the alkali metal phosphate and the alkali metal pyrosulfate can be lithium, sodium, potassium, rubidium and cesium.

It is possible to replace the alkali metal pyrosulfate with a compound which is convertible into the alkali metal pyrosulfate such as an alkali metal hydrogen sulfate, ammonium sulfate or a combination of an alkali metal salt and sulfuric acid. It is also possible to form the alkali metal pyrosulfate in the catalytic oxidation of naphthalene by incorporating sulfur trioxide or a compound which is convertible into sulfur trioxide such as sulfur, sulfur dioxide, hydrogen sulfide, carbon disulfide, trionaphthene, thiophene and mercaptan.

These catalytic components are preferably combined in ranges of 0.1 to 1.0 wt. part of vanadium oxide as $V_2O_5$, 0.1 to 2.0 wt. part of the alkali metal sulfate and/or alkali metal phosphate as a potassium salt and 0.3 to 5.0 wt. part of the alkali metal pyrosulfate as a potassium salt per 1 wt. part of a carrier as silicon oxide.

In the preparation of the catalyst, a press-molding method, a cast molding method, an extrusion molding method or a tabletting molding method can be applied.

The special feature of the catalyst of the present invention is to provide a molded catalyst of a mixture of the carrier and the catalytic components. That is, the mixture of the carrier and the catalytic components is molded and the catalytic components are fused in the vapor phase oxidation of naphthalene. This is different from a catalyst comprising the catalytic components coated on a molded carrier. It is necessary to maintain high durability to impact shock even though the component of the mixture is fused during the vapor phase oxidation of naphthalene.

In order to produce 1,4-naphthoquinone by a vapor phase oxidation of naphthalene, it is preferable to pack a cylindrical catalyst having a pellet diameter of 3 to 10 mm and a through-hole diameter of 1 to 5 mm in a reaction tube having an inner diameter of 19 to 40 mm and to heat the reaction tube at 300° to 450° C. and to carry out the reaction at a temperature of 350° to 550° C. in a concentration of naphthalene of 20 to 50 g./$Nm^3$ air (typical oxygen containing gas) at a space velocity of 1,000 to 5,000 $hr^{-1}$. In order to prolong the catalytic life and to maintain the stability of the reaction, sulfur trioxide or a compound which is convertible to sulfur trioxide such as sulfur, sulfur dioxide, hydrogen sulfide, carbon disulfide, thiophene, thionaphthene or mercaptan can be incorporated into the reaction system.

In the process of the present invention, the catalyst has a special configuration and has the catalytic components mixed with the carrier and most of the catalytic components are fused.

In accordance with the present invention, the catalyst having a configuration having a large outer surface area is used in the vapor phase oxidation of naphthalene, whereby a volume of the feed gas per unit weight or unit volume of the catalyst is greater and the unreacted naphthalene can be minimized and 1,4-naphthoquinone can be obtained at high yield to give high productivity. Therefore, it is remarkably advantageous in an industrial operation.

The present invention will be further illustrated by certain examples and references which are provided for purposes of illustration only and are not intended to be limiting the present invention.

EXAMPLE 1

A mixture of 18.0 g. of silicon oxide, 7.0 g. of ammonium metavanadate, 5.2 g of potassium sulfate and 16.3 g. of potassium hydrogen sulfate was admixed with 25 ml. of water and the mixture was kneaded in a mortar. The mixture was cast-molded in a perforated plate having recesses having a diameter of 4.5 mm in which each projection having a diameter of 1.5 mm is formed to obtain cylindrical pellets having each through-hole. After the cast-molding, the pellets having each through-hole were dried at 100° C. for 3 hours and calcined at 450° C. for 5 hours to obtain the catalyst having each through-hole. After the calcination, the catalyst contained 0.30 wt. part of vanadium pentoxide, 0.31 wt. part of potassium sulfate and 0.81 wt. part of potassium pyrosulfate per 1 wt. part of silicon oxide. Into a glass tube having an inner diameter of 19 mm, 15.9 g. of the catalyst was packed and the surrounding temperature was kept at 385° C. and a mixed gas of air containing naphthalene at a ratio of 41 g. per $Nm^3$ was fed at a rate of 35 Nliter/hr. through the packed catalyst. A conversion of naphthalene was 94.7% (the unreacted naphthalene of 5.3%) and the yield of 1,4-naphthoquinone was 35.6 mol% and the yield of phthalic anhydride was 54.1 mol%.

REFERENCE 1

The kneaded mixture of Example 1 was cast-molded in a perforated plate having recesses having a diameter of 4.5 mm which have not any projection to obtain cylindrical pellets having no throughhole. The pellets were dried and calcined by the process of Example 1 to obtain a catalyst.

In accordance with the process of Example 1 except using 15.9 g. of the catalyst, an oxidation of naphthalene was carried out in the same reaction condition. A conversion of naphthalene was 90.6% (the unreacted naphthalene of 9.4%) and the yield of 1,4-napthoquinone was 32.7 mol%, and the yield of phthalic anhydride was 52.9 mol%.

When a flow rate of the gas was reduced to 31 Nliter/hr., the conversion was increased to 95.0%, but the yield of 1,4-naphthoquinone was 31.6 mol% and the yield of phthalic anhydride was 58.4 mol%.

EXAMPLE 2

A mixture of 3.0 kg. of silicon oxide, 1.26 kg. of ammonium metavanadate and 2.8 kg. of potassium sulfate was thoroughly mixed and admixed with 3 liter of 6.5N-$H_2SO_4$. The mixture was kneaded by a kneader for 15 minutes. The kneaded mixture was dried and pulverized to be less than 20 mesh to obtain a granule. The granule was tabletted into a cylindrical form which has an outer diameter of 5 mm, an inner diameter of 2 mm, a height of 6 mm and a weight of about 175 mg. The tablets were calcined at 450° C. for 5 hours to obtain a catalyst having each through-hole. After the calcination, the catalyst contained 0.33 wt. part of vanadium pentoxide, 0.39 wt. part of potassium sulfate and 0.79 wt. part of potassium pyrosulfate per 1 wt. part of silicon oxide. In a glass tube having an inner diameter of 25 mm, 64 ml. (53.2 g.) of the catalyst was packed and the surrounding temperature was kept at 390° C. and a mixed gas of air containing naphthalene at a ratio of 40 g. per $Nm^3$ was fed at a rate of 96 Nliter/hr. through the packed catalyst. A conversion of naphthalene was 95.2% (the unreacted naphthalene of 4.8%) and the yield of 1,4-naphthoquinone was 33.1 mol% and the yield of phthalic anhydride was 56.0 mol%.

REFERENCE 2

In accordance with the process of Example 2 a catalyst having a cylindrical configuration having an outer diameter of 5 mm, a height of 6 mm and a weight of 200 mg, was prepared.

In accordance with the process of Example 2 except using 64 ml. (64.0 g.) of the catalyst, an oxidation of naphthalene was carried out. A conversion of naphtalene was 87.5% (the unreacted naphthalene of 12.3%) and the yield of 1,4-naphthoquinone was 30.6 mol%, and the yield of phthalic anhydride was 49.6 mol%.

A flow rate of the gas for providing a conversion of naphthalene of 95.2% (the unreacted naphthalene of 4.8%) as the same with that of Example 2 by using the same catalyst was 69 Nliter/hr. The yield of 1,4-naphthoquinone was 29.9 mol% and the yield of phthalic anhydride was 60.1 mol%.

EXAMPLE 3

A mixture of 4.4 kg. of silicon oxide, 1.7 kg. of ammonium metavanadate and 3.8 kg. of potassium sulfate was throughly mixed and admixed with 4 liter of 7.2N-$H_2SO_4$. The mixture kneaded by a kneader for 15 minutes. The resulting kneaded mixture was pulverized and dried and rough grains having greater than 20 mesh was separated to obtain a granule for tabletting. The granule was tabletted to obtain each tablet having a cylindrical configuration having an outer diameter of 5 mm, an inner diameter of 2 mm, a height of 4 mm and a weight of 115 mg.

Into an iron reaction tube having an inner diameter of 25 mm, 1 liter of the catalyst was packed and the gas (air) was fed at a rate of 1.5 $Nm^3$/hr. at 400° C. for 12 hours and then, an oxidation of naphthalene was carried out by feeding air containing naphthalene at a concentration of 40 g./$Nm^3$ at a space velocity of 2,500 $hr^{-1}$ at a surrounding temperature of 400° C. A conversion of naphthalene was 97.8% (the unreacted naphthalene of 2.2%), and the yield of 1,4-naphthoquinone was 33.1 mol% and the yield of phthalic anhydride was 59.5 mol%.

A packed density of the catalyst was 0.82 g./cc. and a gas permeation resistance of the catalytic layer was 255 mmHg at a space velocity of 2,500 $hr^{-1}$.

REFERENCE 3

In accordance with the process of Example 3, a catalyst having a cylindrical configuration having an outer diameter of 5 mm, a height of 4 mm and a weight of 128 mg. was prepared by tabletting the granule.

In accordance with the process of Example 3 except packing 1 liter of the catalyst in the iron reaction tube and feeding the gas at a space velocity of 2,000 $hr^{-1}$, an oxidation of naphthalene was carried out. A conversion of naphthalene was 97.6% (the unreacted naphthalene of 2.4%) and the yield of 1,4-naphthoquinone was 30.5 mol% and the yield of phthalic anhydride was 61.2 mol%. A packed density of the catalyst was 1.00 g./cc. and a gas permeation resistance of the catalyst layer was 258 mmHg at a space velocity of 2,000 $hr^{-1}$.

The gas permeation resistances of the catalyst layers were compared at the ambient temperature. In the case of the catalyst having through-hole, it was 60 mmHg at a rate of 2 $Nm^3$/hr. and 116 mmHg at a rate of 3 $Nm^3$/hr. On the contrary, in the case of the catalyst having no through-hole, it was 84 mmHg at a rate of 2$Nm^3$/hr. and 164 mmHg at a rate of 3 $Nm^3$/hr.

Tests

Each mixture of silicon oxide, ammonium metavanadate, potassium sulfate and potassium hydrogen sulfate of Example 1 was castmolded in a mold having an inner diameter of 10 mm and a thickness of 10, each having 1 to 5 projections for forming through holes of an outer diameter of 1 mm to 6 mm so as to form pellets having an outer diameter of 10 mm and a height of 10 mm and holes as defined in the Table. The pellets were dried and calcined by the process of Example 1. Ten pellets was packed into a glass tube having an inner diameter of 20 mm and the surrounding temperature was kept at 390° C. and a mixed gas containing 40 g. of naphthalene in 1 $Nm^3$ of air was fed at a rate of 15 Nl./hr. The results are as follows:

TABLE

| | Through-holes | | | | | | | |
|---|---|---|---|---|---|---|---|---|
| | Diameter of hole (mm) | | | | | | | |
| | 0 | 1 | 2 | 1 | 2 | 2 | 4 | 6 |
| | Number of holes | | | | | | | |
| | 0 | 3 | 1 | 5 | 2 | 3 | 1 | 1 |
| Ratio of a sectional area of the through-holes to that of the pellet | 0 | 0.03 | 0.04 | 0.05 | 0.08 | 0.12 | 0.16 | 0.36 |
| Ratio of a volume of the holes to the shell | 0 | 0.03 | 0.04 | 0.05 | 0.09 | 0.14 | 0.19 | 0.56 |
| Weight of 10 pellets (g) | 7.4 | 6.4 | 6.4 | 6.3 | 6.3 | 6.1 | 5.6 | 4.4 |
| Conversion (%) | 59 | 64 | 64 | 66 | 66 | 67 | 65 | 63 |
| 1,4-NQ Yield (mol. %) | 24 | 26 | 26 | 27 | 27 | 28 | 28 | 30 |

We claim:

1. A molded catalyst having a cylindrical shape, the outer diameter of the circle being from 3 to 5 mm, the inner diameter of the circle being from 1.0 to 2.5 mm, the thickness of the wall being 1.0 to 1.5 mm and the height being from 4 to 6 mm containing a catalytically effective component useful for oxidizing naphthalene to 1,4-naphthoquinone.

2. A molded catalyst having a cylindrical shape, the outer diameter of the circle being from 3 to 5 mm, the inner diameter of the circle being from 1.0 to 2.5 mm, the thickness of the wall being 1.0 to 1.5 mm and the height being from 4 to 6 mm, said catalyst being prepared using a compression type tabletting machine containing a catalytically effective component useful for oxidizing naphthalene to 1,4-naphthoquinone.

3. A molded catalyst having a cylindrical shape, the outer diameter of the circle being from 45 to 5 mm, the inner diameter of the circle being from 1.5 to 2.5 mm, the thickness of the wall being from 1.0 to 1.5 mm, and the height being from 3 to 6 mm containing a catalytically effective component useful for oxidizing naphthalene to 1,4-naphthoquinone.

4. A molded catalyst having a cylindrical shape, the outer diameter of the circle being from 3 to 6 mm, the inner diameter of the circle being at least 1.0 mm, the thickness of the wall being at most 1.5 mm and the height being from 3 to 6 mm, said catalyst being prepared using a compression type tabletting machine containing a catalytically effective component useful for oxidizing naphthalene to 1,4-naphthoquinone.

5. The molded catalyst of claim 1, wherein said catalytically effective component comprises a mixture of vanadium oxide, an alkali metal compound selected from the group consisting of an alkali metal sulfate, an alkali metal phosphate and a mixture thereof, and an alkali metal pyrosulfate.

6. The molded catalyst of claim 5, wherein said catalytic component comprises vanadium oxide together with a metal oxide selected from the group consisting of oxides of aluminum, tungsten, molybdenum, tin, antimony, titanium, zirconium, chromium, manganese, cobalt, nickel, lead, zinc, niobium, tantalum, cerium, thulium, bismuth, and boron.

7. The molded catalyst of claim 6, wherein the molar ratio of said metal oxide to said vanadium is less than 2.

8. The molded catalyst of claim 5, wherein the alkali metal of said alkali metal sulfate, said alkali metal phosphate and said alkali metal pyrosulfate is selected from the group consisting of lithium, sodium, potassium, rubidium, and cesium.

* * * * *